US008426635B2

(12) United States Patent
Reinhardt et al.

(10) Patent No.: US 8,426,635 B2
(45) Date of Patent: Apr. 23, 2013

(54) PROCESS FOR PREPARING SOLID ALKALINE EARTH METAL SALTS OF SECONDARY PARAFFINSULPHONIC ACIDS

(75) Inventors: Gerd Reinhardt, Kelkheim (DE); Peter Naumann, Taunusstein (DE); Georg Borchers, Bad Nauheim (DE); Mathias Groeschen, Waldbrunn (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 12/921,468

(22) PCT Filed: Mar. 4, 2009

(86) PCT No.: PCT/EP2009/001512

§ 371 (c)(1),
(2), (4) Date: Sep. 15, 2010

(87) PCT Pub. No.: WO2009/112187

PCT Pub. Date: Sep. 17, 2009

(65) Prior Publication Data

US 2011/0021812 A1 Jan. 27, 2011

(30) Foreign Application Priority Data

Mar. 11, 2008 (DE) ........................ 10 2008 013 606

(51) Int. Cl.
*C07C 309/04* (2006.01)

(52) U.S. Cl.
USPC .......................................... 562/115; 562/124

(58) Field of Classification Search .................. 562/115, 562/124
See application file for complete search history.

(56) References Cited

U.S. PATENT DOCUMENTS

| | | | | | |
|---|---|---|---|---|---|
| 2,594,690 | A | * | 4/1952 | Shiffler | 510/536 |
| 3,639,282 | A | * | 2/1972 | Sharman | 562/124 |
| 4,144,226 | A | | 3/1979 | Crutchfield et al. | |
| 4,146,495 | A | | 3/1979 | Crutchfield et al. | |
| 4,680,147 | A | * | 7/1987 | Pistorius | 562/124 |
| 5,318,733 | A | | 6/1994 | Carduck et al. | |
| 5,616,550 | A | | 4/1997 | Kruse et al. | |
| 6,051,544 | A | * | 4/2000 | Lang et al. | 510/446 |
| 2008/0105847 | A1 | | 5/2008 | Lang | |

FOREIGN PATENT DOCUMENTS

| | | |
|---|---|---|
| DE | 26 00 022 | 2/1977 |
| DE | 197 01 896 | 7/1998 |
| EP | 0 030 859 | 6/1981 |
| EP | 0 486 592 | 2/1991 |
| EP | 0 642 576 | 11/1993 |
| GB | 1 498 534 | 1/1978 |
| GB | 1 524 441 | 9/1978 |
| WO | WO 91/02047 | 2/1991 |
| WO | WO 92/11347 | 7/1992 |
| WO | WO 93/23523 | 11/1993 |
| WO | WO 94/23005 | 10/1994 |
| WO | WO 01/44252 | 6/2001 |
| WO | WO 2006/050876 | 5/2006 |

OTHER PUBLICATIONS

International Search Report for PCT/EP2008/003453, dated Nov. 12, 2008.
International Preliminary Report on Patentability for PCT/EP2008/003453, dated Nov. 19, 2009.
English Abstract for WO 92/11347 dated Jul. 9, 1992.
English Abstract for WO 94/23005 dated Oct. 13, 1994.
English Abstract for WO 01/44252 dated Jun. 21, 2001.

* cited by examiner

*Primary Examiner* — Peter G O Sullivan
(74) *Attorney, Agent, or Firm* — Tod A. Waldrop

(57) ABSTRACT

A process for preparing solid alkaline earth metal salts of secondary paraffinsulphonic acids is claimed. This process comprises converting an aqueous solution of a secondary paraffinsulphonic acid and an alkaline earth metal hydroxide into solid form by spray drying.

8 Claims, No Drawings

PROCESS FOR PREPARING SOLID ALKALINE EARTH METAL SALTS OF SECONDARY PARAFFINSULPHONIC ACIDS

The present invention pertains to the synthesis of solid alkaline earth metal salts of secondary paraffinsulfonic acids. The present invention additionally pertains to solid detergents and cleaning products which comprise such alkaline earth metal salts of secondary paraffinsulfonic acids.

Paraffinsulfonic acids (sec. alkanesulfonic acids, SAS) in the form of Na salts are typically used in liquid detergent and cleaning product formulations. These sodium salts of the secondary paraffinsulfonic acid, however, have an extremely high hygroscopicity, thereby making it much more difficult, and in some cases even impossible, to carry out simple isolation and subsequent handling. If the hygroscopic Na salts are used in solid cleaning product formulations (e.g., detergent powders), the result, when the amounts used are above about 5%, is instances of sticking and caking in the end product, hence severely restricting their field of use.

In order to be able nevertheless to offer a solid Na(SAS), specific presentation forms are needed, pellets for example, but cannot be used directly in solid cleaning products on account of excessive particle sizes and unfavorable particle shapes. This is one reason why the majority of the application examples described in the patent literature relate to liquid or gel formulations.

Example 1 of DE-2 600 022 describes liquid detergents and cleaning products which comprise surfactant mixtures made up of semipolar nonionic surfactants and anionic surfactants. Anionic surfactants used are alkaline earth metal salts of anionic surfactants, with paraffinsulfonate included among the anionic surfactants mentioned. As shown by the examples therein, the disclosure there is not of a pure alkaline earth metal salt with paraffinsulfonic acids, but only of a mixture thereof with other surfactants. This is a result of the preparation process, in which a mixture of nonionic and anionic surfactants in the acid form is neutralized. A soluble alkaline earth metal salt is added subsequently. Solid, pulverulent alkaline earth metal salts of secondary alkanesulfonic acids in pure form are not described.

It was an object of the invention, then, to prepare alkaline earth metal salts of secondary paraffinsulfonic acids in pure form. This object has been achieved by subjecting an aqueous solution of paraffinsulfonic acid and alkaline earth metal hydroxide to spray drying.

The invention accordingly provides a process for preparing solid alkaline earth metal salts of secondary paraffinsulfonic acids by converting an aqueous solution of a paraffinsulfonic acid and of an alkaline earth metal salt into a solid form by spray drying.

The secondary paraffinsulfonic acids on which the claimed process is based are known per se. They generally have a chain length of 7 to 20, preferably 8 to 18, carbon atoms. In view of the different valence of alkaline earth metal cation and secondary paraffinsulfonic acid, two different salts may be formed in the relation of $M^{2+}$ to paraffinsulfonic acid, and these salts can be represented in formula terms by $M(SAS)_2$ and M(OH)SAS, with M denoting the alkaline earth metal cation and SAS the paraffinsulfonic acid. By varying the amounts of SAS and/or $M(OH)_2$ it is also possible to prepare products which in terms of their OH content are situated between the formulae $M(SAS)_2$ and M(OH)SAS, an example being a compound of the formula $M(SAS)(SAS)_{0.5}(OH)_{0.5}$.

The paraffinsulfonic acids used as starting compounds can be isolated either by distillation or solvent extraction with lower "alcohols" or with supercritical $CO_2$ from sulfoxidation mixtures of relatively long-chain alkanes. If necessary, the paraffinsulfonic acids may be bleached prior to neutralization, using 30%, 50% or 70% strength hydrogen peroxide. The paraffinsulfonic acids typically have an active compound concentration of 70% to 99%, preferably of 80% to 95%, more preferably of 85% to 95%. The amount of 30% strength hydrogen peroxide needed for bleaching is approximately 1% to 5% by weight, preferably 2% to 3% by weight, based on the paraffinsulfonic acid used. Bleaching takes place at 10 to 30° C., preferably at 15 to 25° C., the bleaching time being 2 to 6 hours, preferably 3 to 5 hours.

The unbleached or bleached paraffinsulfonic acid is subsequently added over the course of about 60 to 120 min at 50 to 60° C. to an aqueous solution of alkaline earth metal hydroxide, preferably magnesium hydroxide, the molar ratio of paraffinsulfonic acid to alkaline earth metal hydroxide being generally 0.8 to 2.5, preferably 1 to 2. Stirring is continued until a stable pH has become established. The $Mg(SAS)_2$ obtained has a pH in the acid range (pH 2-4). This product can subsequently, if needed, be adjusted to a neutral pH with a little sodium hydroxide solution or sodium carbonate. Mg(OH)SAS has a pH of 6 to 9.

The aqueous solution of the salt, produced in this way, is converted into the solid pulverulent alkaline earth metal paraffinsulfonate by removal of the water, by means of spray drying.

Spray drying processes are well known to the skilled worker and can be carried out typically in spraying towers, but also in fluidized-bed apparatus. Typically the material for drying is sprayed in the form of an aqueous solution or slurry from the top of the spraying tower. In order to prepare a spray liquid having favorable properties for the operation, such as viscosity, distribution of solid material in a suspension, for example, it may be necessary to treat the liquid accordingly and/or to add suitable auxiliaries. The spray liquid may be treated, for example, by heat treatment or by passing it through a homogenization step. By adding the auxiliaries it is possible, for example, to influence the distribution of solid material in a spray slurry or else the surface tension.

For the spraying of the liquid there are various systems available, such as single-fluid, two-fluid or multiple-fluid nozzles or atomizer disks, with which fine liquid droplets are produced. Drying is accomplished by hot gas, which is passed in cocurrent or countercurrent through the tower with respect to the direction of spraying. Downstream of the dryer, the dried particles are separated from the gas stream, typically by means of cyclones and/or dust filters. Primary factors affecting the drying procedure, other than the nozzle spraying conditions, are the temperature profile of entry and exit temperatures. In this context it must be ensured that the entry temperature is not too high and the exit temperature is not too low. For the process of the invention, the entry temperature ought in general to be in the range of T=120-220° C., preferably in the range of T=150-200° C. The exit temperature substantially determines the attainable residual moisture content of the powder, and for the process of the invention is situated generally in the range of T=80-120° C., preferably in the range of T=90-110° C.

The alkaline earth metal salts of paraffinsulfonic acids that are prepared in this way are notable for an extremely low hygroscopicity. As a result, they are easier to formulate into a solid presentation form, and are easier to incorporate into solid laundering and cleaning formulations. It is also possible to formulate these salts in the form of powders, granules or else co-granules with other—preferably solid—surfactants.

The alkaline earth metal salts of secondary paraffinsulfonic acids may be employed both with and without the use of a carrier in detergents and cleaning products.

The spray-dried alkaline earth metal salts of secondary paraffinsulfonic acids that are obtained in accordance with the invention are suitable directly for use in detergents and cleaning products. In one particularly preferred form of use, however, they can first be granulated by conventional methods and then provided with a coating shell. For the granulation, consideration may be given in principle to all common methods, such as compacting, agglomerative granulation and mixer granulation, fluidized-bed granulation, extrusion or pelletizing, for example. In accordance with the requirements of the end product and/or the granulating method, it may be necessary to use auxiliaries, additives, other active components, etc.

In the case of the coating step, the granules are coated in a further step with a film-forming substance, thereby allowing the properties of the product to be set specifically or influenced considerably. The coating agent is typically applied in the form of a solution or a melt, or even, in special cases, as a solid. Common methods here are the fluidized bed or suitable mixers, which according to requirements may be operated with downstream drying or cooling. Also conceivable in principle are methods of microencapsulation or matrix encapsulation.

The spray powders obtained in accordance with the invention feature very good storage stability in detergent, cleaning product, and disinfectant formulations in powder form. They are ideal for use in heavy-duty laundry detergents, scouring salts, toilet blocks, and other shaped articles, machine dishwashing detergents, and general-purpose cleaning products in powder form.

The alkaline earth metal salts of secondary paraffinsulfonic acids are used in the detergents and cleaning products at concentrations of 1% to 60%, preferably 2% to 30%, and more particularly 3% to 15%.

The detergents and cleaning products, which may be present in the form of granules, solids in powder or tablet form, or other shaped bodies, may comprise in principle, in addition to the stated alkaline earth metal salts of secondary paraffinsulfonic acids, all known ingredients that are customary in such compositions.

The detergents and cleaning products may especially comprise further surfactants, peroxygen compounds, peroxygen activators or organic peracids, builders, inorganic and organic acids, bases, cleaning enhancers, solvents, hydrotropes, buffers, complexing agents, preservatives, thickeners, skin protection agents, foam regulators, active disinfectant ingredients, enzymes and specific additives with color- or fiber-conserving action. Further assistants such as electrolytes, and colorants and fragrances, are possible.

A cleaning product for hard surfaces may further comprise constituents with abrasive action, especially from the group encompassing quartz flours, wood flours, polymer flours, chalks, and glass microspheres, and mixtures thereof. Abrasives are present in the inventive cleaning products preferably at a level not more than 20% by weight, especially from 5% to 15% by weight.

The detergents and cleaning products may, as well as the inventive alkaline earth metal salts of secondary paraffinsulfonic acids, comprise one or more further surfactants, useful surfactants being especially anionic surfactants, nonionic surfactants and mixtures thereof, but also cationic, zwitterionic and amphoteric surfactants. Such surfactants are present in inventive detergents in proportions of preferably 1% to 50% by weight, especially of 3% to 30% by weight, whereas smaller proportions, i.e. amounts up to 20% by weight, especially up to 10% by weight and preferably in the range from 0.5% to 5% by weight, are normally present in cleaning products for hard surfaces.

Anionic surfactants suitable in addition to the inventive alkaline earth metal salts of secondary paraffinic acids are especially soaps and those which contain sulfate or sulfonate groups. Useful surfactants of the sulfonate type are preferably $C_8$-$C_{18}$-alkylbenzenesulfonates, olefinsulfonates, i.e. mixtures of alkene- and hydroxyalkanesulfonates, and also disulfonates, as obtained, for example, from monoolefins having terminal or internal double bonds by sulfonation with gaseous sulfur trioxide and subsequent alkaline or acidic hydrolysis of the sulfonation products. Also suitable are alkanesulfonates which are obtained from $C_{12}$-$C_{18}$-alkanes, for example by sulfochlorination with subsequent hydrolysis or neutralization. Also suitable are the esters of alpha-sulfo fatty acids (ester sulfonates), for example the alpha-sulfonated methyl esters of hydrogenated coconut fatty acids, palm kernel fatty acids or tallow fatty acids, which are prepared by sulfonating the methyl esters of fatty acids of vegetable and/or animal origin having 8 to 20 carbon atoms in the fatty acid molecule, with subsequent neutralization to form water-soluble monosalts.

Further suitable anionic surfactants are sulfated fatty acid glycerol esters, which are mono-, di- and triesters, and mixtures thereof. Preferred alk(en)yl sulfates are the alkali metal and especially the sodium salts of the sulfuric monoesters of the $C_{12}$-$C_{18}$ fatty alcohols, for example of coconut fatty alcohol, tallow fatty alcohol, lauryl, myristyl, cetyl or stearyl alcohol, or of the $C_8$-$C_{20}$ oxo-process alcohols and those monoesters of secondary alcohols of this chain length. Also preferred are alk(en)yl sulfates of the chain length stated which contain a synthetic, straight-chain alkyl radical prepared on a petrochemical basis. Also suitable are the sulfuric monoesters of the straight-chain or branched alcohols ethoxylated with 1 to 6 mol of ethylene oxide, such as 2-methyl-branched $C_9$-$C_{11}$ alcohols with on average 3.5 mol of ethylene oxide (EO) or $C_{12}$-$C_{18}$ fatty alcohols with 1 to 4 EO.

The preferred anionic surfactants also include the salts of alkylsulfosuccinic acid, which are also referred to as sulfosuccinates or as sulfosuccinic esters, and the mono- and/or diesters of sulfosuccinic acid with alcohols, preferably with fatty alcohols and especially with ethoxylated fatty alcohols. Preferred sulfosuccinates contain $C_8$-$C_{18}$ fatty alcohol radicals or mixtures of these. Useful further anionic surfactants include fatty acid derivatives of amino acids, for example of N-methyltaurine (taurides) and/or of N-methylglycine (sarcosinates). Useful further anionic surfactants include especially soaps, for example in amounts of 0.2% to 5% by weight. Especially suitable are saturated fatty acid soaps, such as the salts of lauric acid, myristic acid, palmitic acid, stearic acid, hydrogenated erucic acid and behenic acid, and also especially soap mixtures derived from natural fatty acids, for example coconut, palm kernel or tallow fatty acids.

The anionic surfactants, including the soaps, which are present in addition to the inventive alkaline earth metal salts of secondary paraffinic acids, may be present in the form of their sodium, potassium or ammonium salts, and as soluble salts of organic bases, such as mono-, di- or triethanolamine. The anionic surfactants are preferably present in the form of their sodium or potassium salts, especially in the form of the sodium salts. Anionic surfactants are present in inventive detergents preferably in amounts of 0.5% to 50% by weight and especially in amounts of 5% to 25% by weight.

The nonionic surfactants used are preferably alkoxylated, advantageously ethoxylated, especially primary alcohols having preferably 8 to 18 carbon atoms and on average 1 to 12 mol of ethylene oxide (EO) per mole of alcohol, in which the alcohol radical may be linear or preferably 2-methyl-branched, or may contain linear and methyl-branched radicals in a mixture, as typically present in oxo-process alcohol radicals. However, especially preferred are alcohol ethoxylates having linear radicals from alcohols of native origin having 12 to 18 carbon atoms, for example from coconut, palm, tallow fat or oleyl alcohol, and on average 2 to 8 EO per mole of alcohol. The preferred ethoxylated alcohols include, for example, $C_{12}$-$C_{14}$ alcohols with 3 EO or 4 EO, $C_9$-$C_{11}$ alcohols with 7 EO, $C_{13}$-$C_{15}$ alcohols with 3 EO, 5 EO, 7 EO or 8 EO, $C_{12}$-$C_{18}$ alcohols with 3 EO, 5 EO or 7 EO and mixtures of these, such as mixtures of $C_{12}$-$C_{14}$ alcohol with 3 EO and $C_{12}$-$C_{18}$ alcohol with 7 EO. The degrees of ethoxylation specified constitute statistical averages which may be an integer or a fraction for a specific product. Preferred alcohol ethoxylates have a narrow homolog distribution (narrow range ethoxylates, NRE). In addition to these nonionic surfactants, fatty alcohols with more than 12 EO may also be used. Examples thereof are (tallow) fatty alcohols with 14 EO, 16 EO, 20 EO, 25 EO, 30 EO or 40 EO.

The nonionic surfactants also include alkylpolyglycosides of the general formula $RO(G)_x$ in which R is a primary, straight-chain or methyl-branched, especially 2-methyl-branched, aliphatic radical having 8 to 22, preferably 12 to 18, carbon atoms, and G is a glycoside unit having 5 or 6 carbon atoms, preferably glucose. The degree of oligomerization x which specifies the distribution of monoglycosides and oligoglycosides is an arbitrary number, which may also assume fractional values as a quantity to be determined analytically, between 1 and 10; x is preferably 1.2 to 1.4. Likewise suitable are polyhydroxy fatty acid amides of the formula (I) in which the $R^1CO$ radical is an aliphatic acyl radical having 6 to 22 carbon atoms, $R^2$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups.

(I)

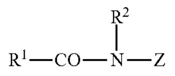

(II)

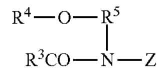

The polyhydroxy fatty acid amides preferably derive from reducing sugars having 5 or 6 carbon atoms, especially from glucose. The group of the polyhydroxy fatty acid amides also includes compounds of the formula (II) where $R^3$ is a linear or branched alkyl or alkenyl radical having 7 to 12 carbon atoms, $R^4$ is a linear, branched or cyclic alkylene radical or an arylene radical having 2 to 8 carbon atoms and $R^5$ is a linear, branched or cyclic alkyl radical or an aryl radical, or an oxyalkyl radical having 1 to 8 carbon atoms, preference being given to $C_1$-$C_4$ alkyl or phenyl radicals, and [Z] is a linear polyhydroxyalkyl radical whose alkyl chain is substituted by at least two hydroxyl groups, or alkoxylated, preferably ethoxylated or propoxylated, derivatives of this radical. [Z] is obtained here too preferably by reductive amination of a sugar such as glucose, fructose, maltose, lactose, galactose, mannose or xylose. The N-alkoxy- or N-alyloxy-substituted compounds may then be converted to the desired polyhydroxy fatty acid amides by reaction with fatty acid methyl esters in the presence of an alkoxide as a catalyst.

A further class of nonionic surfactants used with preference, which may be used either as the sole nonionic surfactant or in combination with other nonionic surfactants, especially together with alkoxylated fatty alcohols and/or alkylglycosides, is that of alkoxylated, preferably ethoxylated or ethoxylated and propoxylated, fatty acid alkyl esters, preferably having 1 to 4 carbon atoms in the alkyl chain, especially fatty acid methyl esters. Nonionic surfactants of the amine oxide type, for example N-cocoalkyl-N,N-dimethylamine oxide and N-tallowalkyl-N,N-dihydroxyethylamine oxide, and of the fatty acid alkanolamide type may also be suitable.

Useful further surfactants include what are known as gemini surfactants. This generally refers to those compounds which have two hydrophilic groups per molecule. These groups are generally separated from one another by a “spacer”. This spacer is generally a carbon chain which should be long enough that the hydrophilic groups have a sufficient separation and they can act independently of one another. Such surfactants generally feature an unusually low critical micelle concentration and the ability to greatly reduce the surface tension of water. However, it is also possible to use gemini polyhydroxy fatty acid amides or polypolyhydroxy fatty acid amides. Further surfactant types may have dendrimeric structures.

Suitable peroxidic bleaches are hydrogen peroxide and compounds which release hydrogen peroxide under the laundering and cleaning conditions, such as alkali metal peroxides, organic peroxides such as urea-hydrogen peroxide adducts, and inorganic persalts such as alkali metal perborates, percarbonates, perphosphates, persilicates, persulfates and peroxynitrites. Mixtures of two or more of these compounds are likewise suitable. Particular preference is given to sodium perborate tetrahydrate and especially sodium perborate monohydrate, and also sodium percarbonate. Sodium perborate monohydrate is preferred owing to its good storage stability and its good solubility in water. Sodium percarbonate may be preferred for ecological reasons.

Hydroperoxides are a further suitable group of peroxide compounds. Examples of these substances are cumene hydroperoxide and t-butyl hydroperoxide.

Aliphatic or aromatic mono- or dipercarboxylic acids and the corresponding salts are also suitable as peroxy compounds. Examples thereof are peroxynaphthoic acid, peroxylauric acid, peroxystearic acid, N,N-phthaloylaminoperoxycaproic acid (PAP), 1,12-diperoxydodecanedioic acid, 1,9-diperoxyazelaic acid, diperoxysebacic acid, diperoxyisophthalic acid, 2-decyldiperoxybutane-1,4-dioic acid and 4,4'-sulfonylbisperoxy-benzoic acid.

In the detergents and cleaning products, it is also possible for suitable bleach activators to be present in the customary amounts (about 1% to 10% by weight).

Suitable bleach activators are organic compounds having an O-acyl or N-acyl group, especially from the group of the activated carboxylic esters, especially sodium nonanoyloxybenzenesulfonate, sodium isononanoyloxy-benzenesulfonate, sodium 4-benzoyloxybenzenesulfonate, sodium trimethylhexanoyioxybenzenesulfonate, carboxylic anhydrides, especially phthalic anhydride, acylated polyhydric alcohols, especially triacetin, ethylene glycol diacetate, 2,5-diacetoxy-2,5-dihydrofuran, lactones, acylals, carboxamides, acylated ureas and oxamides, N-acylated hydantoins, for example 1-phenyl-3-acetyl hydantoin, hydrazides, triazoles, hydrotriazines, urazoles, diketopiperazides, sulfurylamides, polyacylated alkylenediamines, for example N,N,N',N'-tetraacetylethylenediamine (TAED), acylated triazine derivatives, especially 1,5-diacetyl-2,4-dioxohexahydro-1,3,5-triazine, acylated glycolurils, especially tetraacetylglycoluril, N-acylimides, especially N-nonanoylsuccinimide, and acylated sugar derivatives, especially pentaacetylglucose (PAG), pentaacetylfructose, tetraacetylxylose and octaacetyllactose, and also acetylated, optionally N-alkylated glucamine and gluconolactone, and/or N-acylated lactams, for example N-benzoylcaprolactam, but also nitrile compounds, for example quaternary trialkylammonionitrile salts, especially the cyanomethyltrimethylammonium salt, but also heterocyclically substituted quaternary nitrile compounds.

In addition to the conventional bleach activators listed above or in their stead, it is also possible for sulfonimines, open-chain or cyclic quaternary iminium compounds such as dihydroisoquinolinium quats or dihydroisoquinolinium betaines and/or bleach-boosting transition metal salts or mono- or polynuclear transition metal complexes with acyclic or macrocyclic ligands to be present.

Suitable organic and inorganic builders are neutral or especially alkaline salts which can precipitate or complex calcium ions. Suitable builder substances which are in particular ecologically uncontroversial are crystalline sheet-type silicates of the formula $NaMSi_{(x)}O_{(2x+1)}$ where M is sodium or hydrogen, x is 1.9 to 22, preferably 1.9 to 4, and y is 0 to 33, for example Na—SKS-5 ($\alpha$-$Na_2Si_2O_5$), Na—SKS-7 ($\beta$-$Na_2Si_2O_5$, natrosilite), Na—SKS-9 ($NaHSi_2O_5*H_2O$), Na—SKS-10 ($NaHSi_2O_3*3H_2O$, kanemite), Na—SKS-11 (t-$Na_2Si_2O_5$) and Na—SKS-13 ($NaHSi_2O_5$), but especially Na—SKS-6 ($\delta$-$Na_2Si_2O_5$), and also finely crystalline synthetic water-containing zeolites, especially of the NaA type, which have a calcium binding capacity in the range from 100 to 200 mg CaO/g.

Zeolites and sheet silicates may be present in an amount of up to 60% by weight in the product.

Additionally suitable are non-neutralized or partly neutralized (co)polymeric polycarboxylic acids. These include the homopolymers of acrylic acid or of methacrylic acid or copolymers thereof with further ethylenically unsaturated monomers, for example acrolein, dimethylacrylic acid, ethylacrylic acid, vinylacetic acid, allylacetic acid, maleic acid, fumaric acid, itaconic acid, meth(allylsulfonic acid), vinylsulfonic acid, styrenesulfonic acid, acrylamidomethylpropanesulfonic acid, and monomers containing phosphorus groups, for example vinylphosphoric acid, allylphosphoric acid and acrylamidomethylpropanephosphoric acid and salts thereof, and also hydroxyethyl (meth)acrylate sulfate, allyl alcohol sulfate and allyl alcohol phosphates.

Preferred (co)polymers have an average molar mass of 1000 to 100 000 g/mol, preferably of 2000 to 75 000 g/mol and especially of 2000 to 35 000 g/mol.

The degree of neutralization of the acid groups is advantageously 0% to 90%, preferably 10% to 8.0% and especially 30% to 70%.

The suitable polymers include in particular also homopolymers of acrylic acid and copolymers of (meth)acrylic acid with maleic acid or maleic anhydride.

Further suitable copolymers derive from terpolymers which can be obtained by polymerizing 10% to 70% by weight of monoethylenically unsaturated dicarboxylic acids having 4 to 8 carbon atoms, salts thereof, 20% to 85% by weight of monoethylenically unsaturated monocarboxylic acids having 3 to 10 carbon atoms or salts thereof, 1% to 50% by weight of monounsaturated monomers which, after hydrolysis, release hydroxyl groups on the polymer chain, and 0% to 10% by weight of further free-radically copolymerizable monomers.

Likewise suitable are graft polymers of monosaccharides, oligosaccharides, polysaccharides and modified polysaccharides, and also animal or vegetable proteins.

Preference is given to copolymers of sugar and other polyhydroxyl compounds and a monomer mixture composed of 45% to 96% by weight of monoethylenically unsaturated $C_3$ to $C_{10}$ monocarboxylic acids or mixtures of $C_3$ to $C_{10}$ monocarboxylic acids and/or salts thereof with monovalent cations, 4% to 55% by weight of monomers containing monoethylenically unsaturated monosulfonic acid groups, monoethylenically unsaturated sulfuric esters, vinylphosphoric esters and/or the salts of these acids with monovalent cations, and 0% to 30% by weight of water-soluble unsaturated compounds which have been modified with 2 to 50 mol of alkylene oxide per mole of monoethylenically unsaturated compounds.

Further suitable polymers are polyaspartic acid and derivatives thereof in non-neutralized or only partly neutralized form.

Also particularly suitable are graft polymers of acrylic acid, methacrylic acid, maleic acid and further ethylenically unsaturated monomers onto salts of polyaspartic acid, as typically obtained in the above-described hydrolysis of the polysuccinimide. It is possible here to dispense with the otherwise necessary addition of acid for the preparation of the only partly neutralized form of the polyaspartic acid. The amount of polyaspartate is typically selected such that the degree of neutralization of all carboxyl groups incorporated in the polymer does not exceed 80%, preferably 60%.

Further usable builders are, for example, the carboxylic acids used preferably in the form of their sodium salts, such as citric acid, especially trisodium citrate and trisodium citrate dihydrate, nitrilotriacetic acid and its water-soluble salts; the alkali metal salts of carboxymethyloxysuccinic acid, ethylenediaminetetraacetic acid, mono-, dihydroxysuccinic acid, $\alpha$-hydroxy-propionic acid, gluconic acid, mellitic acid, benzopolycarboxylic acids and those as disclosed in U.S. Pat. No. 4,144,226, and U.S. Pat. No. 4,146,495.

Also suitable are phosphate-containing builders, for example alkali metal phosphates, which may be present in the form of their alkaline, neutral or acidic sodium or potassium salts.

Examples thereof are trisodium phosphate, tetrasodium diphosphate, disodium dihydrogenphosphate, pentasodium triphosphate, so-called sodium hexametaphosphate, oligomeric trisodium phosphate with degrees of oligomerization in the range from 5 to 1000, especially 5 to 50, and mixtures of sodium and potassium salts.

These builder substances may be present at from 5% to 80% by weight; preference is given to a proportion of 10% to 60% by weight.

It is likewise possible to use complexing agents, such as ethane-1-hydroxy-1,1-diphosphonate and other known phosphonates.

In addition, the inventive products may comprise volatile alkalizing compounds. These include ammonia and/or $C_{1-9}$-alkanolamines. Preferred alkanolamines are ethanolamines, particular preference being given to monoethanolamine.

Cleaning products may additionally also comprise organic acids such as acetic acid, glycolic acid, lactic acid, citric acid, succinic acid, adipic acid, malic acid, tartaric acid and gluconic acid, preference being given to acetic acid, citric acid and lactic acid, particular preference to acetic acid.

Inventive acidic cleaning product formulations may especially inorganic acids, for example mineral acids such as phosphoric acid, sulfuric acid, nitric acid or hydrochloric acid, but also amidosulfonic acid. Additionally suitable are organic acids, preferably short-chain aliphatic mono-, di- and tricarboxylic acids, hydroxycarboxylic acids and dicarboxylic acids. Examples of aliphatic monocarboxylic acids and dicarboxylic acids are $C_1$-$C_6$ alkyl and alkenyl acids, such as glutaric acid, succinic acid, propionic acid, adipic acid, maleic acid, formic acid and acetic acid. Examples of hydroxycarboxylic acids include hydroxyacetic acid and citric acid. It is also possible to use sulfonic acids of the formula $R—SO_3H$ which contain a straight-chain or branched and/or cyclic or unsaturated $C_1$-$C_{32}$ hydrocarbon radical R, for example $C_{6-22}$-alkanesulfonic acids, $C_{6-22}$-α-alkanesulfonic acids, $C_{6-22}$-α-olefinsulfonic acids and $C_{1-22}$-alkyl-$C_{6-10}$-arylsulfonic acids, for example $C_{1-22}$-alkylbenzenesulfonic acids or $C_{1-22}$-alkylnaphthalenesulfonic acids, preferably linear $C_{8-16}$-alkylbenzenesulfonic acids. Particular preference is given to citric acid, acetic acid, formic acid and amidosulfonic acid.

In principle, useful organic solvents are all mono- or polyhydric alcohols. Preference is given to using alcohols having 1 to 4 carbon atoms, such as methanol, ethanol, propanol, isopropanol, straight-chain and branched butanol, glycerol and mixtures of the alcohols mentioned. Further preferred alcohols are polyethylene glycols having a relative molecular mass below 2000. Preference is given especially to use of polyethylene glycol having a relative molecular mass between 200 and 600 and in amounts up to 45% by weight, and of polyethylene glycol having a relative molecular mass between 400 and 600 in amounts of 5 to 25% by weight. An advantageous mixture of solvents consists of monomeric alcohol, for example ethanol, and polyethylene glycol in a ratio of 0.5:1 to 1.2:1.

Further suitable solvents are, for example, triacetin (glyceryl triacetate) and 1-methoxy-2-propanol.

The thickeners used are preferably hydrogenated castor oil, salts of long-chain fatty acids, which are used preferably in amounts of 0% to 5% by weight and especially in amounts of 0.5% to 2% by weight, for example sodium stearate, potassium stearate, aluminum stearate, magnesium stearate and titanium stearate, or the sodium and/or potassium salts of behenic acid, and also polysaccharides, especially xanthan gum, guar-guar, agar-agar, alginates and tyloses, carboxymethylcellulose and hydroxyethylcellulose, and also relatively high molecular weight poly-ethylene glycol mono- and diesters of fatty acids, polyacrylates, polyvinyl alcohol and polyvinylpyrrolidone, and also electrolytes such as sodium chloride and ammonium chloride.

Suitable thickeners are water-soluble polyacrylates which are crosslinked, for example, with about 1% of a polyallyl ether of sucrose and which have a relative molecular mass of above one million. Examples thereof are the polymers obtainable under the name Carbopol® 940 and 941. The crosslinked polyacrylates are used in amounts of not more than 1% by weight, preferably in amounts of 0.2% to 0.7% by weight.

The enzymes optionally present in inventive products include proteases, amylases, pullulanases, cellulases, cutinases and/or lipases, for example proteases such as BLAP®, Optimase®, Opticlean®, Maxacal®, Maxapem®, Durazym®, Purafect® OxP, Esperase® and/or Savinase®, amylases such as Termamy®, Amylase-LT, Maxamyl®, Duramyl®, Purafectel OxAm, cellulases such as Celluzyme®, Carezyme®, K-AC® and/or the cellulases and/or lipases disclosed by the international patent applications WO 96/34108 and WO 96/34092, such as Lipolase®, Lipomax®, Lumafast® and/or Lipozym®. The enzymes used may, as described, for example, in the international patent applications WO 92/111347 or WO 94/23005, be adsorbed on carriers and/or embedded in coating substances in order to protect them from premature inactivation. They are present in the inventive detergents and cleaning products preferably in amounts of up to 10% by weight, especially of 0.05% to 5% by weight, particular preference being given to the use of enzymes stabilized against oxidative degradation.

Inventive machine dishwasher detergents preferably comprise the customary alkali carriers, for example alkali metal silicates, alkali metal carbonates and/or alkali metal hydrogencarbonates. The customarily used alkali carriers include carbonates, hydrogencarbonates and alkali metal silicates having a molar $SiO_2/M_2O$ ratio (M=alkali metal atom) of 1:1 to 2.5:1. Alkali metal silicates may be present in amounts of up to 40% by weight, especially 3% to 30% by weight, based on the overall product. The alkali carrier system used with preference in inventive cleaning products is a mixture of carbonate and hydrogencarbonate, preferably sodium carbonate and sodium hydrogencarbonate, which may be present in an amount of up to 50% by weight, preferably 5% to 40% by weight.

In a further embodiment of inventive products for the automatic washing of dishware, 20% to 60% by weight of water-soluble organic builders, especially alkali metal citrate, 3% to 20% by weight of alkali metal carbonate and 3% to 40% by weight of alkali metal disilicate are present.

In order to bring about silver corrosion protection, it is possible to use silver corrosion inhibitors in inventive cleaning products for dishware. Preferred silver anticorrosives are organic sulfides such as cystine and cysteine, di- or trihydric phenols, optionally alkyl- or aryl-substituted triazoles such as benzotriazole, isocyanuric acid, and salts and/or complexes of titanium, zirconium, hafnium, molybdenum, vanadium or cerium.

When the products foam too vigorously on use, it is possible also to add to them up to 6% by weight, preferably about 0.5% to 4% by weight, of a foam-regulating compound, preferably from the group encompassing silicones, paraffins, paraffin-alcohol combinations, hydrophobized silicas, fatty acid bisamides and mixtures thereof, and other known commercially available foam inhibitors. The foam inhibitors, especially silicone- and/or paraffin-containing foam inhibitors, are preferably bound to a granular carrier substance soluble or dispersible in water. Special preference is given to mixtures of paraffins and bistearylethylenediamide. Further optional ingredients in the inventive products are, for example, perfume oils.

Useful salts or standardizers include, for example, sodium sulfate, sodium carbonate or sodium silicate (waterglass).

To set a desired pH which does not arise automatically through the mixing of the remaining components, the inventive products may comprise system- and environment-compatible acids, especially citric acid, acetic acid, tartaric acid, malic acid, lactic acid, glycolic acid, succinic acid, glutaric acid and/or adipic acid, but also mineral acids, especially sulfuric acid or alkali metal hydrogensulfates, or bases, especially ammonium or alkali metal hydroxides. Such pH regulators are present in the inventive products preferably at not more than 10% by weight, especially from 0.5% to 6% by weight.

The inventive products are preferably in the form of pulverulent, granular or tableted preparations and other shaped bodies which can be produced in a known manner, for example by mixing, granulating, roll compacting and/or by spray drying the thermally stressable components, and mixing in the more sensitive components, which include especially enzymes, bleaches and the bleach catalyst.

For the production of particulate products with increased bulk density, especially in the range from 650 g/l to 950 g/l, preference is given to a process which has an extrusion step and is disclosed by the European Patent EP 0 486 592. A further preferred production method with the aid of a granulation process is described in the European Patent EP 0 642 576. Inventive products in the form of nondusting, storage-stable free-flowing powders and/or granules having high bulk densities in the range from 800 to 1000 g/l can also be produced by mixing, in a first process stage, the builder components with at least a portion of liquid mixture components while increasing the bulk density of this premixture, and subsequently, if desired after an intermediate drying, combining the further constituents of the product, including the cationic, nitrilic activator, with the premixture thus obtained.

To produce inventive products in tablet form, the procedure is preferably to mix all constituents with one another in a mixer and to compress the mixture by means of conventional tablet presses, for example eccentric presses or rotary presses. In this way, tablets which are fracture-resistant and nevertheless sufficiently rapidly soluble under use conditions and have flexural strengths of normally above 150 N are obtained without any problem. A tablet produced in this way preferably has a weight of 1.5 g to 40 g, especially of 20 g to 30 g, at a diameter of 3-5 mm to 40 mm.

A further preferred embodiment comprises formulations in piece form, which can be used for improving odor and cleaning in toilet bowls (so-called toilet blocks), comprising, in addition to the inventive alkaline earth metal salts of secondary paraffinsulfonic acids, a further 15% to 30% by weight of anionic and/or nonionic surfactants, preferably fatty alkyl sulfates, alkylbenzenesulfonates, alkylpolyglucosides, fatty alkyl ether sulfates, fatty alkyl ethoxylates, 10% to 40% by weight of organic solvent, 5% to 15% by weight of one or more acids or salts thereof, for example formic acid, acetic acid, amidosulfonic acid, sodium hydrogensulfate, coconut fatty acids, 0% to 5% by weight of complexing agents, for example sodium citrate or sodium phosphonate, 0% to 60% by weight of builders, for example sodium sulfate, and 0% to 5% by weight of colorants, fragrances and disinfectants, and also water.

A further preferred embodiment comprises pulverulent formulations which can be used for cleaning toilets (known as toilet cleaning powders), comprising, in addition to the inventive alkaline earth metal salts of secondary paraffinsulfonic acids, a further 15% to 30% by weight of anionic and/or nonionic surfactants, preferably fatty alkyl sulfates, fatty alkyl ethoxylates, alkylbenzenesulfonates, alkylpolyglucosides, fatty alkyl ether sulfates, 10% to 50% by weight of acid, preferably formic acid, acetic acid, citric acid, amidosulfonic acid, potassium or sodium hydrogel sulfate, 0% to 5% by weight of complexing agent, 0% to 10% by weight of assistants and fillers, preferably sodium carbonate, 0% to 5% by weight of colorants, fragrances and disinfectants, and also water.

A further preferred embodiment comprises cleaning product pieces in block or tablet form, which can be used for cleaning and rinsing of solid surfaces, for example dishware, floors, windows, or else of textiles, comprising, in addition to the inventive alkaline earth metal salts of secondary paraffinsulfonic acids, a further 0% to 25% by weight of anionic and/or nonionic surfactants, preferably fatty alkyl sulfates, alkylbenzenesulfonates, alkylpolyglucosides, fatty alkyl ether sulfates, betaines, amine oxides, alpha-olefinsulfonates, 10% to 40% by weight of organic solvent, 0% to 5% by weight of colorants, fragrances and disinfectants, and also water.

In addition to the ingredients already mentioned, the detergents and cleaning products may comprise any of the conventional additives in amounts typically found in such products.

The examples which follow are intended to illustrate the subject matter of the invention in detail, without restricting it thereto.

EXAMPLES

Example 1

Synthesis of Mg(OH)SAS 141.2 g (0.42 mol) of a 90.8% strength paraffinsulfonic acid were initially taken and were cooled to 15-20° C. Then, at this temperature, 2.8 g of $H_2O_2$ (30%) were added dropwise and the mixture was stirred for 4 hours thereafter, the internal temperature continuing to be 15 to 20° C. This bleached paraffinsulfonic acid was thereafter added dropwise to an aqueous solution of 17.5 g (0.3 mol) of $Mg(OH)_2$ in 280 g of water, which was heated at 50° C. After 90 minutes, the addition was at an end, and a pH of 6.5 had become established. Over the course of 10 hours, a further 2.7 g (0.01 mol) of paraffinsulfonic acid were added, producing a stable pH of 7.6, and the SAS/$Mg(OH)_2$ molar ratio was 1.44. The resultant product solution was clear and readily pourable.

Analytical Data:

Active substance content (for 329.3 g/mol): 32.2%

Water content (Karl-Fischer): 67.1%

Example 2

Synthesis of $Mg(SAS)_2$ 141.2 g (0.42 mol) of a 90.8% strength paraffinsulfonic acid were initially taken and were cooled to 15 to 20° C. Then, at this temperature, 2.8 g of $H_2O_2$ (30%) were added dropwise and the mixture was stirred for 4 hours thereafter, the internal temperature continuing to be 15 to 20° C. This bleached paraffinsulfonic acid was thereafter added dropwise to an aqueous solution of 11.2 g (0.21 mol) of $Mg(OH)_2$ in 280 g of water, which was heated at 60° C. After 60 minutes, the addition was at an end, and a pH of 1.2 had become established. The resulting product solution was clear and readily pourable.

Analytical Data:

Active substance content (for 329.3 g/mol): 30.2%

Water content (Karl-Fischer): 71.4%

Example 3

Spray Drying of Magnesium Paraffinsulfonate Solutions

The magnesium paraffinsulfonate solutions of examples 1 and 2 were used to produce dried, solid salts of paraffinsulfonic acid. The solutions were sprayed in a laboratory spray dryer (model: Büchi B 191 mini spray dryer), an entry temperature of T=200° C. being selected. Setting a liquid metering rate of about 3-5 g/min resulted in an exit temperature of about 117-124° C. The end product in each case was a dry, flowable spray powder which had a residual moisture content of about 5.3% (infrared dryer, 120° C.). The average particle size of the spray powder was about 5-7 μm (method: laser diffraction; Malvern Mastersizer).

In a further experimental setting, the aqueous solution was spray dried with an entry temperature of T=145° C. and a metering rate of about 3.5 to 4 g/min, producing an exit temperature of 88 to 92° C. Here again, the product was dry and flowable with a residual moisture content of about 4.3%.

Magnesium paraffinsulfonate powder obtained in this way proved to be insensitive in a hygroscopicity test. In spite of absorbing a certain amount of water, the material remained mechanically stable and after the end of the test was in the form of a dry, flowable powder.

Comparative Example

Spray Drying of a Sodium Paraffinsulfonate Solution

A 30% strength aqueous solution of the sodium paraffinsulfonate prepared by diluting a 60% product (Hostapur SAS 60—commercial product of Clariant) was used to produce a dried salt of paraffinsulfonic acid. The solution was sprayed in a laboratory spray dryer (model: Büchi B 191 mini spray dryer), the initial entry temperature selected being T=160° C. The liquid metering rate was set at about 4 g/min, producing a dryer exit temperature which was measured to be T=106° C. Under these conditions, however, no spray powder was isolated in the collecting vessel of the cyclone. In order to produce a dry sodium paraffinsulfonate in spite of this, the dryer entry temperature was then raised gradually up to T=190° C. Since, in the course of the experiment, there was, first, still no spray powder separated off on the cyclone, and, second, the walls of the dryer were coated with a sticky moist layer of the product, the trial was terminated without success. It was not possible to carry out spray drying of salts of paraffinsulfonic acid based on potassium or ammonium.

The invention claimed is:

1. A process for preparing solid alkaline earth metal salts of secondary paraffinsulfonic acids, comprising the step of spray drying an aqueous solution, wherein the aqueous solution comprises at least one secondary paraffinsulfonic acid and at least one alkaline earth metal hydroxide to form a solid.

2. The process as claimed in claim 1, wherein a secondary paraffinsulfonic acid has 7 to 20 carbon atoms.

3. The process as claimed in claim 1, wherein the secondary paraffinsulfonic acid has an active compound concentration of 70% to 99%.

4. The process as claimed in claim 1, wherein the secondary paraffinsulfonic acid has an active compound concentration of 85% to 95%.

5. The process as claimed in claim 1, further comprising the step of bleaching the secondary paraffinsulfonic acid prior to mixing with the alkaline earth metal hydroxide to form the aqueous solution.

6. The process as claimed in claim 1, wherein the molar ratio of secondary paraffinsulfonic acid to alkaline earth metal hydroxide is 0.8-2.5.

7. The process as claimed in claim 1, wherein the molar ratio of secondary paraffinsulfonic acid to alkaline earth metal hydroxide is 1.0-2.0.

8. A detergent, cleaning product or disinfectant comprising a solid alkaline earth metal salt of secondary paraffinic acids prepared by the process as claimed in claim 1.

* * * * *